US010945699B2

United States Patent
Ye et al.

(10) Patent No.: US 10,945,699 B2
(45) Date of Patent: Mar. 16, 2021

(54) RESPIRATORY SOUND ANALYSIS FOR LUNG HEALTH ASSESSMENT

(71) Applicant: Hill-Rom Services PTE Ltd., Singapore (SG)

(72) Inventors: Chau Chong Ye, Singapore (SG); Yue Wang, Singapore (SG); Suresha Venkataraya, Singapore (SG); Aye Aung, Singapore (SG); Zhon Chu, Skaneateles Falls, NY (US); Aaron R. Burnham, Skaneateles Falls, NY (US); Matthew D. Mullin, Memphis, NY (US)

(73) Assignee: Hill-Rom Services PTE Ltd., Singapore (SG)

( * ) Notice: Subject to any disclaimer, the term of this patent is extended or adjusted under 35 U.S.C. 154(b) by 480 days.

(21) Appl. No.: 15/849,864

(22) Filed: Dec. 21, 2017

(65) Prior Publication Data
US 2018/0177483 A1 Jun. 28, 2018

Related U.S. Application Data

(60) Provisional application No. 62/439,565, filed on Dec. 28, 2016, provisional application No. 62/531,113, filed on Jul. 11, 2017.

(51) Int. Cl.
*A61B 7/00* (2006.01)
*A61B 5/08* (2006.01)
(Continued)

(52) U.S. Cl.
CPC ............ *A61B 7/003* (2013.01); *A61B 5/0015* (2013.01); *A61B 5/08* (2013.01); *A61B 5/0803* (2013.01);
(Continued)

(58) Field of Classification Search
CPC ......... A61B 7/003; A61B 5/0015; A61B 5/08; A61B 5/6805; A61B 5/4833;
(Continued)

(56) References Cited

U.S. PATENT DOCUMENTS 2,764,020 A * 9/1956 Gadd ...................... G01H 11/02
73/661
3,483,861 A * 12/1969 Tiep ...................... A61B 5/1135
600/534
(Continued)

FOREIGN PATENT DOCUMENTS

EP 2 737 920 A1 6/2014

OTHER PUBLICATIONS

Marques, A. et al., "Are crackles an appropriate outcome measure for airway clearance therapy?", http://www.ncbi.nlm.nih.gov/pubmed/22348337, Respir Care. Sep. 2012; Epub Feb. 17, 2012, Copyright 2012 Daedalus Enterprises, 2 pages.
(Continued)

*Primary Examiner* — Rachel T Sippel
*Assistant Examiner* — Kelsey E Baller
(74) *Attorney, Agent, or Firm* — Merchant & Gould P.C.

(57) ABSTRACT

A respiratory acoustic analysis system for sensing and analyzing respiratory sounds of a patient may include a High Frequency Chest Wall Oscillation (HFCWO) vest, at least one sensor coupled with the HFCWO vest, and an algorithm stored in a processor for processing sensed data from the at least one acoustic sensor to provide processed data describing the respiratory sounds of the patient, in a form that can be used by a physician or other user.

15 Claims, 14 Drawing Sheets

(51) Int. Cl.
*A61H 9/00* (2006.01)
*A61B 5/00* (2006.01)
*A61H 23/00* (2006.01)
*A61B 5/113* (2006.01)
*A61M 16/00* (2006.01)
*A61H 31/00* (2006.01)

(52) U.S. Cl.
CPC .......... *A61B 5/4833* (2013.01); *A61B 5/6805* (2013.01); *A61H 9/0007* (2013.01); *A61H 23/004* (2013.01); *A61H 23/006* (2013.01); *A61H 31/00* (2013.01); *A61M 16/0051* (2013.01); *A61B 5/0816* (2013.01); *A61B 5/1135* (2013.01); *A61B 5/7267* (2013.01); *A61B 2562/0204* (2013.01); *A61H 2023/002* (2013.01); *A61H 2201/1207* (2013.01); *A61H 2201/165* (2013.01); *A61H 2201/1619* (2013.01); *A61H 2201/1621* (2013.01); *A61H 2201/1623* (2013.01); *A61H 2201/1626* (2013.01); *A61H 2201/1645* (2013.01); *A61H 2201/501* (2013.01); *A61H 2201/5005* (2013.01); *A61H 2201/5043* (2013.01); *A61H 2201/5076* (2013.01); *A61H 2205/084* (2013.01); *A61H 2230/405* (2013.01); *A61M 16/0006* (2014.02)

(58) Field of Classification Search
CPC ... A61B 5/0803; A61B 5/1135; A61B 5/0816; A61B 5/7267; A61B 9/0007; A61M 16/00; A61M 16/003; A61M 16/0006; A61M 16/0051; G01H 11/00; G01H 11/02; G01H 11/06; G10K 15/043; G10K 11/18; G10K 11/24; G10K 11/26; G10K 9/12; A61H 21/00; A61H 23/00; A61H 23/004; A61H 23/006; A61H 23/008; A61H 23/02; A61H 9/0007; A61H 31/00; A61H 2201/1621; A61H 2201/5005; A61H 2201/1645; A61H 2201/1619; A61H 2201/1626; A61H 2201/1623; A61H 2201/5076; A61H 2201/1207; A61H 2201/501; A61H 2201/165; A61H 2023/002
USPC .......................................................... 73/632
See application file for complete search history.

(56) References Cited

U.S. PATENT DOCUMENTS

| | | | | |
|---|---|---|---|---|
| 5,235,967 | A * | 8/1993 | Arbisi | A61H 23/0218 601/101 |
| 6,168,568 | B1 * | 1/2001 | Gavriely | A61B 5/087 600/529 |
| 6,254,556 | B1 * | 7/2001 | Hansen | A61H 9/0078 137/565.16 |
| 6,340,025 | B1 | 1/2002 | Van Brunt | |
| 6,349,724 | B1 * | 2/2002 | Burton | F04D 25/166 128/204.18 |
| 7,011,637 | B2 * | 3/2006 | Sherman | A61H 31/00 601/41 |
| 7,747,051 | B2 * | 6/2010 | Zhang | G06T 7/0012 382/128 |
| 8,052,626 | B2 | 11/2011 | Huster et al. | |
| 8,460,223 | B2 | 6/2013 | Huster et al. | |
| 8,663,138 | B2 | 3/2014 | Huster et al. | |
| 8,734,370 | B1 * | 5/2014 | Ignagni | A61H 9/0078 601/149 |
| 9,237,982 | B2 | 1/2016 | Van Brunt | |
| 10,518,048 | B2 * | 12/2019 | Bobey | A61M 16/0006 |
| 2002/0032386 | A1 * | 3/2002 | Sackner | A61B 5/0205 600/536 |
| 2003/0199945 | A1 * | 10/2003 | Ciulla | A61F 5/56 607/48 |
| 2004/0097850 | A1 * | 5/2004 | Plante | A61H 23/0236 601/41 |
| 2007/0027367 | A1 * | 2/2007 | Oliver | A61B 5/0002 600/300 |
| 2008/0000477 | A1 * | 1/2008 | Huster | A61B 34/25 128/204.23 |
| 2008/0108914 | A1 | 5/2008 | Brouqueyre et al. | |
| 2008/0281219 | A1 | 11/2008 | Glickman et al. | |
| 2011/0087143 | A1 * | 4/2011 | Bobey | A61B 7/003 600/586 |
| 2012/0022415 | A1 | 1/2012 | Mullen et al. | |
| 2012/0035514 | A1 | 2/2012 | Huster et al. | |
| 2012/0071777 | A1 * | 3/2012 | MacAuslan | A61B 5/0823 600/529 |
| 2012/0119920 | A1 | 5/2012 | Sallop et al. | |
| 2013/0158435 | A1 * | 6/2013 | Endo | A61B 7/003 600/586 |
| 2013/0289456 | A1 * | 10/2013 | Chang Guo | A61H 9/0078 601/149 |
| 2014/0005579 | A1 * | 1/2014 | Drlik | A61H 23/0218 601/111 |
| 2014/0257151 | A1 | 9/2014 | Chikkanaravangala et al. | |
| 2014/0276271 | A1 * | 9/2014 | Stryker | A61H 23/04 601/46 |
| 2015/0366751 | A1 * | 12/2015 | Stemple | A61H 23/006 601/44 |
| 2016/0213560 | A1 | 7/2016 | Sturdivant | |
| 2016/0317383 | A1 | 11/2016 | Stanfield et al. | |
| 2016/0324487 | A1 * | 11/2016 | Guo | G08B 21/0269 |
| 2017/0094216 | A1 * | 3/2017 | Ekambaram | H04N 5/232 |
| 2017/0119255 | A1 * | 5/2017 | Mahajan | A61B 5/6823 |
| 2019/0142686 | A1 * | 5/2019 | Lee | A61H 23/006 601/44 |
| 2019/0170208 | A1 * | 6/2019 | Liu | F16F 15/005 |

OTHER PUBLICATIONS

Khan, S. I., "Respiratory Sound Analysis for Identifying Lung Diseases: A Review," http://www.ijsr.net/archive/v3i11/T0NUMTQ5NzU%3D.pdf, International Journal of Science and Research (IJSR), vol. 3 Issue 11, Nov. 2014, 6 pages.

Murphy, R. L. et al., "Automated lung sound analysis in patients with pneumonia," http://www.ncbi.nlm.nih.gov/pubmed/15571639, Respir Care. Dec. 2004, 2 pages.

Gurung, Arati et al., "Computerized Lung Sound Analysis as diagnostic aid for the detection of abnormal lung sounds: a systematic review and meta-analysis," http://www.ncbi.nlm.nih.gov/pmc/articles/PMC3227538/, Respir Med. Sep. 2011, 8 pages.

Göğüş, Fatma Z. et al., "Classification of Asthmatic Breath Sounds by Using Wavelet Transforms and Neural Networks," http://www.ijsps.com/uploadfile/2014/1210/20141210043302655.pdf, International Journal of Signal Processing Systems vol. 3, No. 2, Dec. 2015, 6 pages.

Sengupta, Nandini, et al., "Lung sound classification using cepstral-based statistical features," http://cs.joensuu.fi/~sahid/Sahidullah_files/CBM-2016.pdf, Reprint submitted to Computers in Biology and Medicine Jun. 9, 2016, 34 pages.

Wang, Hong et al., "Lung Sound/Noise Separation for Anesthesia Respiratory Monitoring," http://www.wseas.us/e-library/conferences/miami2004/papers/484-321.pdf, 2004, 6 pages.

* cited by examiner

RESPIRATORY SOUND ANALYSIS FOR LUNG HEALTH ASSESSMENT

RELATED APPLICATIONS

This patent application claims the benefit of U.S. Patent Application Ser. No. 62/439,565 filed on Dec. 28, 2016 and U.S. Patent Application Ser. No. 62/531,113 filed on Jul. 11, 2017, the entireties of which are hereby incorporated by reference.

BACKGROUND

Many chronic and acute respiratory conditions result in retained respiratory secretions that patients cannot clear from their airways without assistance. A number of airway clearance systems using vests worn by the patient have been developed. These vest-based systems use high frequency chest wall oscillation (HFCWO) technology to assist in airway clearance for patients suffering from airway dysfunction, secretion retention and/or ineffective cough or secretion clearance due to immobility, deconditioning or muscle weakness. Patients with obstructive pulmonary diseases, for example, such as cystic fibrosis (CF), may wear an HFCWO vest to perform airway clearance therapy (ACT) for secretion removal every day at home. If not removed from the lungs, retained secretions may contribute to increased rates of respiratory infection, hospitalization, and reduced lung function.

Typically, an HFCWO vest is prescribed to a respiratory patient by a physician or other care provider. Each vest device is preset with a specific therapy setting, according to the assessment of the patient's lung condition by the physician, and the therapy setting cannot be modified by the patient. If the patient's lung function changes, as it often does, the physician typically has no way of learning of this change. The patient will typically continue to use the vest device, which provides the same therapy that was prescribed originally by the care provider, despite any changes in lung function. Unfortunately, it is often critically important to change the therapy setting of the vest, to provide the right therapy for the patient's changing lung function. Current vest systems, however, generally do not allow for such changes to be made without having the patient return to the care giver's office, pulmonology clinic, hospital or similar facility. If the old therapy continues to be administered to the changed lungs, the patient's condition may worsen, thus leading to reduced clearing of the lung and possible infection or other problems. Also, current HFCWO vest systems generally do not provide a way for a remote physician to monitor or analyze a patient's lung condition. Thus, the efficacy of the ACT cannot be measured. Early intervention and modification of ACT with an HFCWO vest system will likely help reduce readmission rates and total medical costs for the patient and the health care system.

Therefore, although currently available HFCWO vest systems may be effective for many patients, there is still a need to provide improved HFCWO vest systems. Ideally, such systems would allow for individualized therapies that are customizable for each unique patient. Also ideally, such systems would allow physicians and other care givers to monitor lung function of patients and provide instructions for adjusting the HFCWO vest systems to accommodate for changes in lung function. At least some of these objectives will be addressed by the embodiments described herein.

BRIEF SUMMARY

Respiratory sound provides important information regarding the present condition of the lung. Auscultation, the process of listening to internal sounds of the human body using a stethoscope or microphone, has been an effective tool for the diagnosis of lung abnormalities and lung disorders since at least 1816, when Rene Laennec invented the stethoscope. Recording respiratory sounds may, thus, be very helpful for evaluating and monitoring a patient's respiratory condition. The various embodiments described herein include an HFCWO vest with one or more microphones for recording patient respiratory sounds. The microphone(s) record respiratory sounds and transmit sound signals to a portal, control unit, the cloud, or other location away from the HFCWO vest and the patient. A backend server or other processor may perform pre-processing and feature extraction of the collected sound signals and may then provide this information to one or more data mining algorithms.

Various embodiments of a respiratory sound analysis system may use one or more machine learning algorithms to allow a computer to make decisions based on the previous experiences, by analyzing historical data sets, such as lung sound databases. A neural network is one example that uses a machine learning algorithm for feature recognition and classification to classify different lung sounds. Computerized lung sound analysis may provide objective evidence for identifying different lung diseases. Similarly, CF patient respiratory sound data may be collected before and after ACT and processed to assess patient lung condition. Thus, the efficacy of the therapy can be evaluated. The combination of this lung information, patient progress reports, and other information, such as but not limited to therapy settings, compliance reports, usage reports, and the like, may be used to develop a personalized care and care management solution, and to determine the best therapy settings.

In one aspect of the present disclosure, a respiratory therapy and analysis system for administering a percussive treatment and sensing and analyzing respiratory sounds of a patient may include a high frequency chest wall oscillation (HFCWO) vest, at least one sensor coupled with the HFCWO vest, and an algorithm stored in a processor for processing sensed data from the sensor to provide processed data describing the respiratory sounds of the patient, in a form that can be used by a physician or other user. In various embodiments, the sensor(s) may include a microphone, a pressure transducer and/or a voice coil actuator. For example, one embodiment includes multiple pairs of voice coil actuators, where each pair includes a transmitter voice coil actuator on one side of the HFCWO vest and a receiver voice coil actuator on an opposite side of the HFCWO vest. The pairs of voice coil actuators are configured to provide the percussive treatment to the patient and also to sense respiratory function in the form of phase shifts.

In some embodiments, the system's algorithm comprises a machine learning algorithm. The algorithm may include a pre-processing function, a feature extraction function, and a classification function. In various embodiments, the form of the processed data may be a patient progress report, a pulmonary function test report and/or weather or other environmental data that may affect breathing. In some embodiments, the system may further include a charger main control board coupled with the sensor, which may include a digital signal processor and a radiofrequency module.

In another aspect of the present disclosure, a respiratory analysis system for sensing and analyzing respiratory sounds of a patient may include a smart adapter for attaching to an HFCWO vest, at least one acoustic sensor housed in the smart adapter, and an algorithm stored in a processor for processing sensed acoustic data from the acoustic sensor to provide processed data describing the respiratory sounds of the patient, in a form that can be used by a physician or other user. In some embodiments, the processor is housed in the smart adapter. In some embodiments, the system also includes an application for a smart device, configured to display at least one indicator to the patient regarding a lung function of the patient's lungs and/or progress of a lung treatment being performed on the patient's lungs.

In another aspect of the present disclosure, a method for measuring and analyzing respiratory sounds of a patient's lungs may involve sensing respiratory sounds and/or chest wall movement, using at least one sensor coupled with an HFCWO vest, converting sensed data from the patient's lungs to electronic data, processing the electronic data to provide lung function assessment data, and providing the lung function assessment data to a user. In some embodiments, the sensing step involves transmitting a signal from a transmitter voice coil actuator on one side of the HFCWO vest and receiving the signal with a receiver voice coil actuator on an opposite side of the HFCWO vest. In such an embodiment, the processing step may involve measuring a phase shift between the transmitted signal and the received signal. In some embodiments, the sensing step involves sensing chest wall movement with the transmitter voice coil activator and/or the receiver voice coil activator, and the providing step involves providing a respiratory rate.

In some embodiments, the method may also involve automatically stopping a percussive therapy provided by the HFCWO vest, based on the lung function assessment data. Such an embodiment may also involve determining if clarity of the patient's breathing is at or above a predetermined threshold clarity, where the percussive therapy is stopped when the clarity is at or above the predetermined threshold clarity. Some embodiments optionally involve providing a visual indicator to signal to stop the therapy when a determination is made that the lungs are clear. Some other embodiments optionally also involve providing an adjusted HFCWO treatment prescription, based on the lung function assessment data. Some embodiments also involve displaying the lung function assessment data on a display of a smart device.

These and other aspects and embodiments are described in further detail below, in reference to the attached drawing figures.

DETAILED DESCRIPTION

Figure 1:
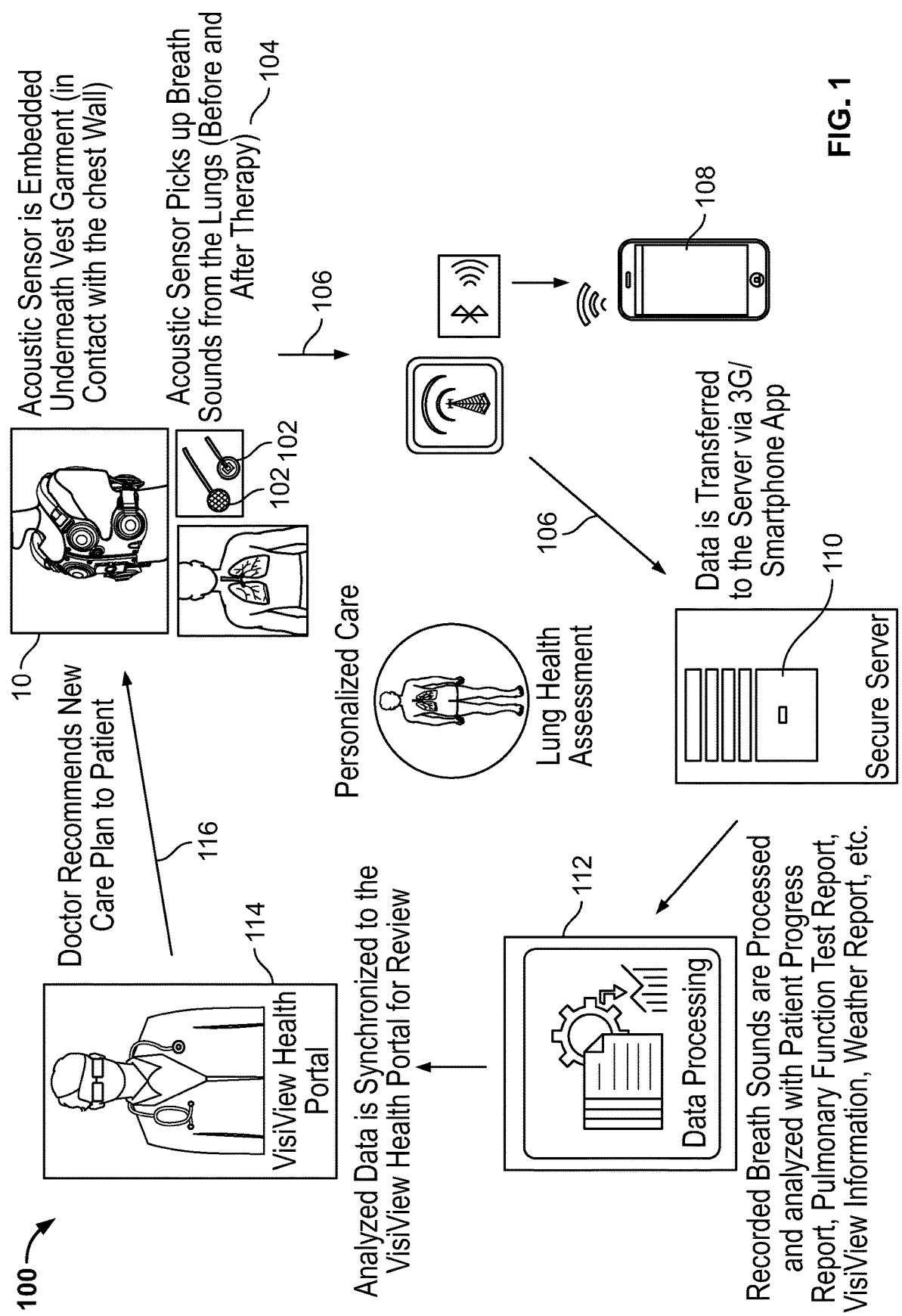
FIG. 1 is a diagram illustrating a system a high frequency chest wall oscillation (HFCWO) and respiratory sound analysis system and data flow, according to one embodiment.

The embodiments of the claimed subject matter and the various features and advantageous details thereof are explained more fully with reference to the non-limiting embodiments and examples that are described and/or illustrated in the accompanying drawings and detailed in the following description. The features illustrated in the drawings are not necessarily drawn to scale, and features of one embodiment may be employed with other embodiments, even if not explicitly stated herein. Descriptions of well-known components and processing techniques may be briefly mentioned or omitted, so as to not unnecessarily obscure the embodiments of the claimed subject matter described. The examples used herein are intended merely to facilitate an understanding of ways in which the claimed subject matter may be practiced and to further enable those of skill in the art to practice the embodiments of the claimed subject matter described herein. Accordingly, the examples and embodiments herein are merely illustrative and should not be construed as limiting the scope of the claimed subject matter, which is defined solely by the appended claims and applicable law. Moreover, like reference numerals may represent similar parts throughout the several views of the drawings.

The present application is generally directed to a system and method including an HFCWO device, an acoustic sensor (or multiple sensors), and a processor for analyzing data from the acoustic sensor(s). The HFCWO device, as well as the system and method, may be used in the treatment of any suitable respiratory disease or condition, one example of which is cystic fibrosis (CF). Although the example of CF may be used frequently herein, this use is for exemplary purposes only and should not be interpreted as limiting the scope of the application.

FIG. 1 illustrates a respiratory sound analysis system 100 and method for acquiring acoustic respiratory data using an HFCWO vest device 10 with one or more attached acoustic sensors 102 and processing the data to adjust an Airway Clearance Therapy (ACT) treatment administered by the HFCWO vest device 10. In various embodiments, any suitable HFCWO vest device 10 may be used. In this embodiment, for example, HFCWO device 10 is a pneumatic device, and an HFCWO controller (not shown in FIG. 1) is configured to control the supply of gas to HFCWO device 10, thereby controlling compressive force on the chest wall of the user. In other embodiments, HFCWO device 10 may be of any type, including but not limited to any combination of mechanical, pneumatic, hydraulic and/or electrical components, to provide chest wall oscillation therapy. Further descriptions of embodiments of HFCWO devices and controllers may be found, for example, in U.S. Pat. No. 8,052,626 and U.S. Patent Application Publication No. 2012/0035514, both of which are hereby incorporated by reference herein.

One or more acoustic sensors 102, such as but not limited to voice coil actuators ("VCAs"), pressure transducers or microphones, may be attached to or embedded in HFCWO vest device 10. For example, in some embodiments multiple acoustic sensors may be attached to an inner surface of HFCWO vest 10, in positions to contact a patient's chest wall and thus effectively capture acoustic signals from the patient's lungs during respiration. In one embodiment, for example, multiple pairs of VCAs may be embedded in (or attached to) HFCWO vest device 10, such that one VCA of each pair is on the front of the vest and one VCA of each pair is on the back of the vest. In such embodiments, the VCA pairs provide percussion therapy to the patient's chest, and also sense lung function. One VCA of each pair acts as a transmitter, and the other VCA acts as a receiver. In some embodiments, the VCAs of each pair may also switch functions from receiver to transmitter and vice versa. One embodiment of vest device 10 may include two pairs of VCAs, while other embodiments may include one, three, four or any other suitable numbers of pairs. Some of these embodiments are described in further detail below. In alternative embodiments, any other types and numbers of suitable acoustic sensors 102 may be used in HFCWO vest device 10.

A first step in the method of using the system 100 depicted in FIG. 1 to analyze breath sounds may involve receiving breath sounds (or "respiratory sounds") from the lungs 104, with acoustic sensors 102 in HFCWO vest device 10. Sensors 102 may receive breath sounds for any suitable length of time, such as continuously before and after ACT is administered by HFCWO vest 10. For all of the embodiments described below, breath sounds may be sensed before, during and/or after treatment.

In the next step of the method, sensed acoustic data may be transmitted 106 from acoustic sensor(s) 102 to a server 110, portal, the cloud, or other processor, via a wireless communication device 108, such as a smartphone, tablet or the like. Server 110 or other processor may then perform pre-processing and feature extraction of the collected sound signals and may then provide this information to one or more data processing algorithms 112, such as data mining algorithms. Algorithms 112 are used to provide analyzed/processed data in the form of a report, notes, alert, text message, email or other usable form of information for a physician 114 or other care provider. Examples of such information include but are not limited to a patient progress report, a pulmonary function test report, weather or other environmental data that may affect breathing, and/or the like. The processed data is then provided to the physician or other care provider 114, who can use the information to adjust the ACT therapy 116 delivered by the HFCWO device 10. In some embodiments, for example, the processed information may be available on a portal, which the physician can access to review the information.

Various alternative embodiments of methods for sensing and analyzing breath sounds are described in greater detail below. In different embodiments, breath sounds may be sensed and/or analyzed in different ways. For example, breath sounds may be analyzed to monitor respiratory rate in some embodiments or alternatively may be analyzed to detect coughing or wheezing or a combination thereof. Information generated by sensing and analyzing breath sounds may also be used for any of a number of different purposes. Two examples of these are for providing information to physicians and/or others, so that treatment can be monitored and adjusted as needed, and providing information back to the HCFWO vest device 10, so that it can automatically adjust a treatment as needed, based on the feedback information. Some embodiments may use the information for both purposes—informing the physician and also providing closed-loop feedback to automatically adjust the HCFWO vest device 10. Again, at least some details of various alternative embodiments are described in further detail below.

Various embodiments of respiratory sound analysis system 100 may use one or more machine learning algorithms to allow a computer (including a processor and tangible computer-readable memory encoding instructions thereon for execution by the processor) to make decisions based on the previous experiences, by analyzing historical data sets, such as lung sound databases. A neural network is one example that uses a machine learning algorithm for feature recognition and classification to classify different lung sounds. Computerized lung sound analysis may provide objective evidence for identifying different lung diseases. Similarly, CF patient respiratory sound data may be collected before and after ACT and processed to assess patient lung condition. Thus, the efficacy of the therapy can be evaluated. The combination of this lung information, patient progress reports, and other information, such as but not limited to therapy settings, compliance reports, usage reports, and the like, may be used to develop a personalized care and care management solution, and to determine the best therapy settings.

Figure 2:
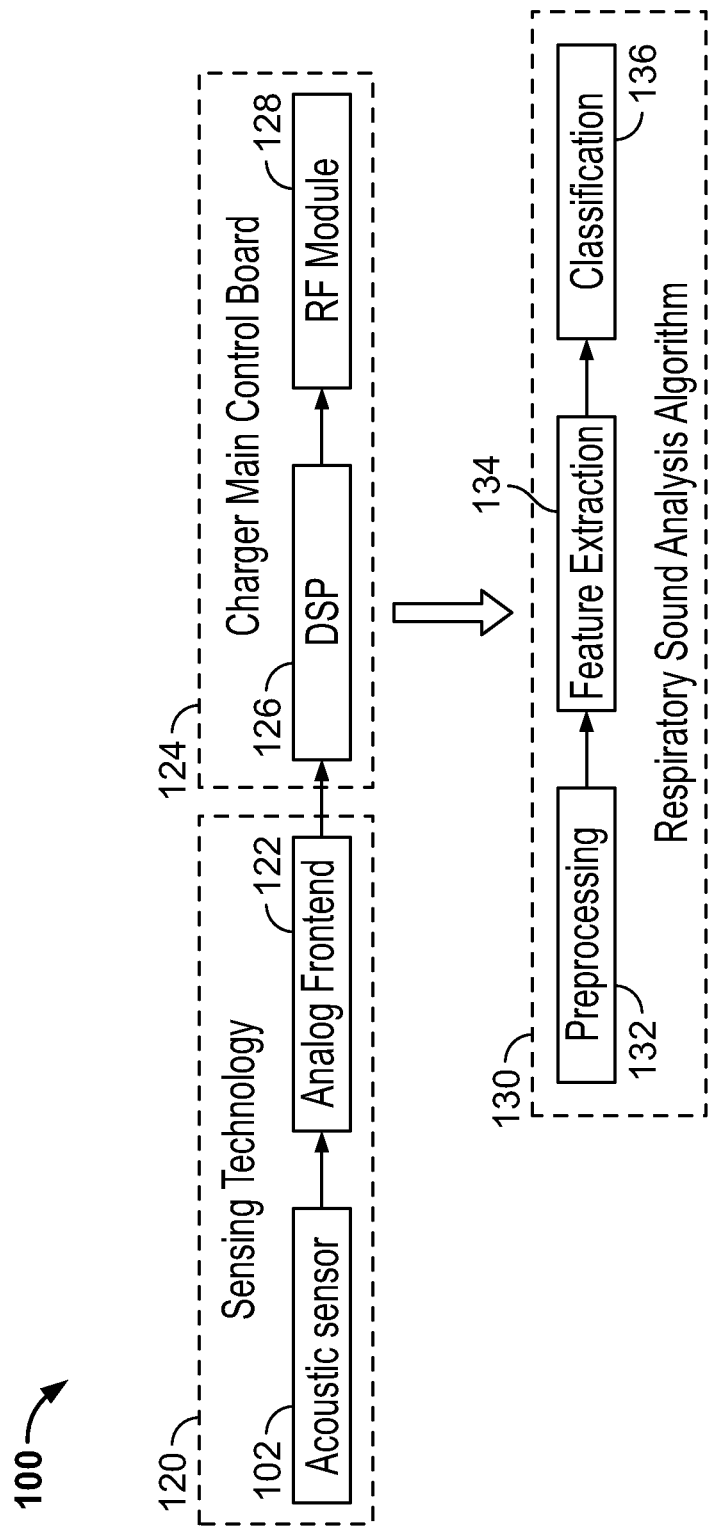
FIG. 2 is a diagram of a portion of the HFCWO and respiratory sound analysis system of FIG. 1.

FIG. 2 is a more detailed diagram of the sensing and processing technology of respiratory acoustic analysis system 100, according to one embodiment. This portion respiratory acoustic analysis system 100 includes three primary components: sensing technology 120; a charger main control board 124; and a respiratory sound analysis algorithm 130. Sensing technology 120 may include one or more VCAs, pressure transducers, microphones or other acoustic sensors 102, as mentioned previously, and an analog front end 122 (e.g., an analog-to-digital signal converter). Sensed data travels from sensing technology 120 to charger main control board 124, which may include a digital signal processor (DSP) 126 and a radiofrequency (RF) module 128. Data next travels from charger main control board 124 to respiratory sound analysis algorithm 130, which may include a preprocessing step 132, a feature extraction step 134 and a classification step 136. Preprocessing 132 may include a band pass filter, for example in the range of 150 Hz to 2000 Hz, a time-split blind channel identification, and a recorder for recording ambient sound for noise cancellation. Feature extraction 134 may include wavelet transforms and a cepstral-based statistic. Classification 136 may include computerized lung sound analysis for detection of abnormal lung sounds, classification of breath sounds using wavelet transforms and neural networks, and/or the like.

Figure 3:
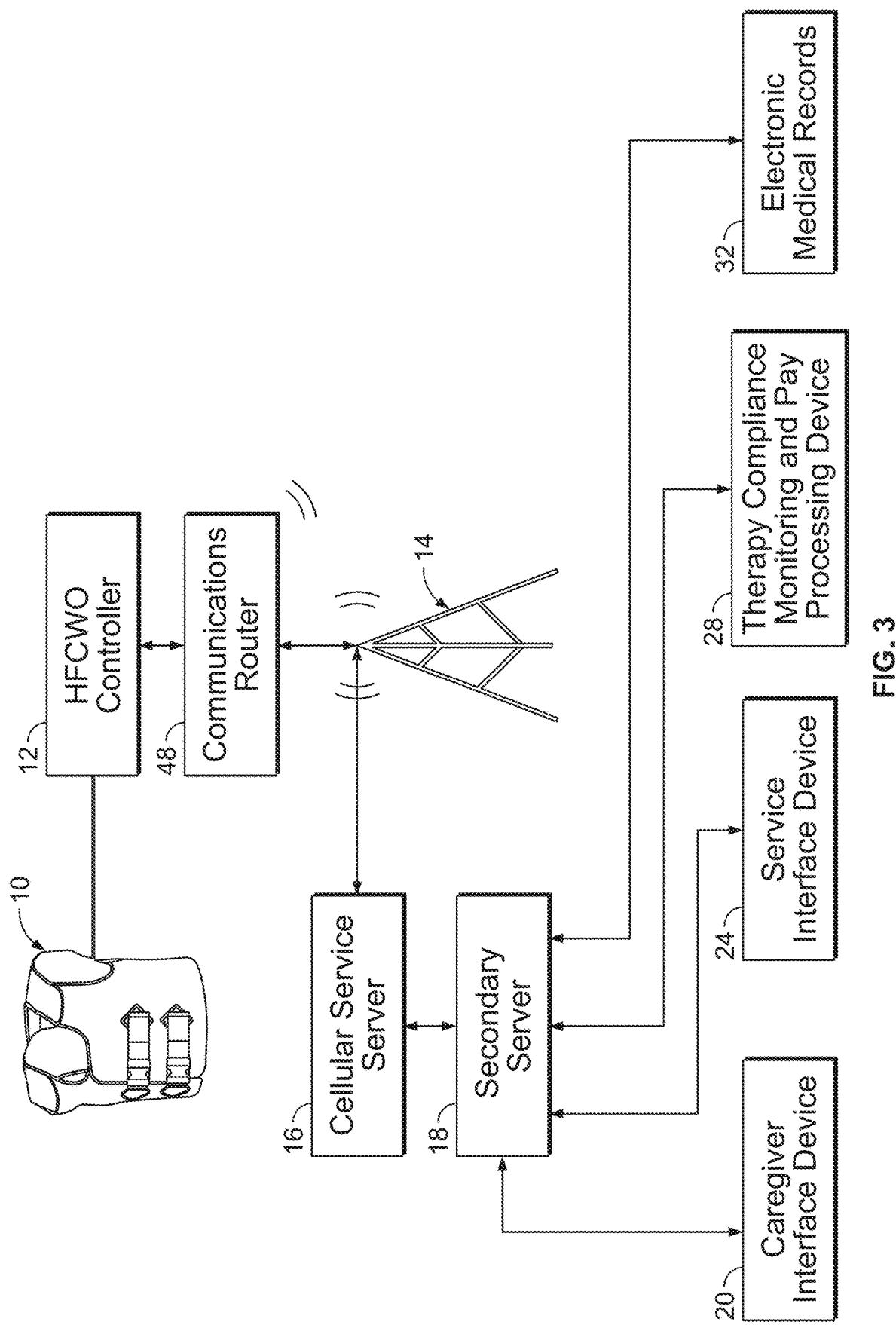
FIG. 3 is a diagram of an HFCWO data connectivity system, according to one embodiment.

FIG. 3 shows HFCWO device 10 configured to be controlled by an HFCWO controller 12. The HFCWO controller 12 is configured to communicate with a communications router 48. In this embodiment, the HFCWO controller 12 is configured to communicate with the communications router 48 via a wireless connection, while in another embodiment, the HFCWO controller 12 is configured to communicate with a communications router 48 via a wired connection. In this embodiment, the HFCWO controller 12 is configured to communicate with the communications router 48 using Bluetooth technology, while in other embodiments, the HFCWO controller 12 may communicate with the communications router 48 using any protocol and/or technology including but not limited to ZigBee. In other embodiments, the HFCWO controller 12 may communicate with the communications router 48 using any radio frequency signal.

The communications router 48 is configured to communicate with a cellular service server 16 via a cellular connection in the embodiment shown in FIG. 3. In this embodiment, the communications router 48 is configured to communicate with the cellular service server 16 via a connection through a cellular tower 14. In another embodiment, any number of cellular towers may relay information between the communications router 10 and the cellular service server 16. In another embodiment, the communications router 10 is configured to communicate with the cellular service server 16 via any combination of data transfer between communications satellites and/or cellular towers. Cellular service server 16 is a computer in this embodiment, while in other embodiments, the cellular service server 16 may be any computing device configured to communicate with the communications router 48 via a cellular connection. The cellular service server 16 is configured to transfer at least a portion of data received from the communications router 48 to a secondary server 18. Secondary server 18 is configured to transmit data to a caregiver interface device 20, service interface device 24, therapy compliance monitoring and pay processing device 28 and electronic medical records (EMR) 32, in this embodiment. The caregiver interface device 20 is a computer in this embodiment and is configured to display indications of HFCWO therapy as well as allow a caregiver to control operating parameters of the HCFWO therapy which are then transmitted to the HFCWO controller 12 via the secondary server 18, cellular service server 16 and communications router 48. Data transmitted from the secondary server 18 to the service interface device 24, which is a computer in this embodiment, allows a service technician to be alerted of need for scheduled and/or unscheduled maintenance. The therapy compliance monitoring and pay processing device 28 is a computer in this embodiment and is configured to determine compliance of HFCWO therapy relative to a prescribed routine. Information regarding adherence of a prescribed protocol and/or use of HFCWO device is used for determination of insurance reimbursements and/or pay processing for services rendered in this embodiment. Data from the secondary server 18 is also logged in an electronic medical record (EMR) 32 in this embodiment.

While the caregiver interface device 20, service interface device 24, therapy compliance monitoring and pay processing device 28 and electronic medical record (EMR) 32 are cited as computers in the embodiment shown in FIG. 3, in other embodiments, they may be any combination of a display and any type of computing device including but not limited to PDAs, phones, tablets, smart watches and smart glasses.

Figure 4:
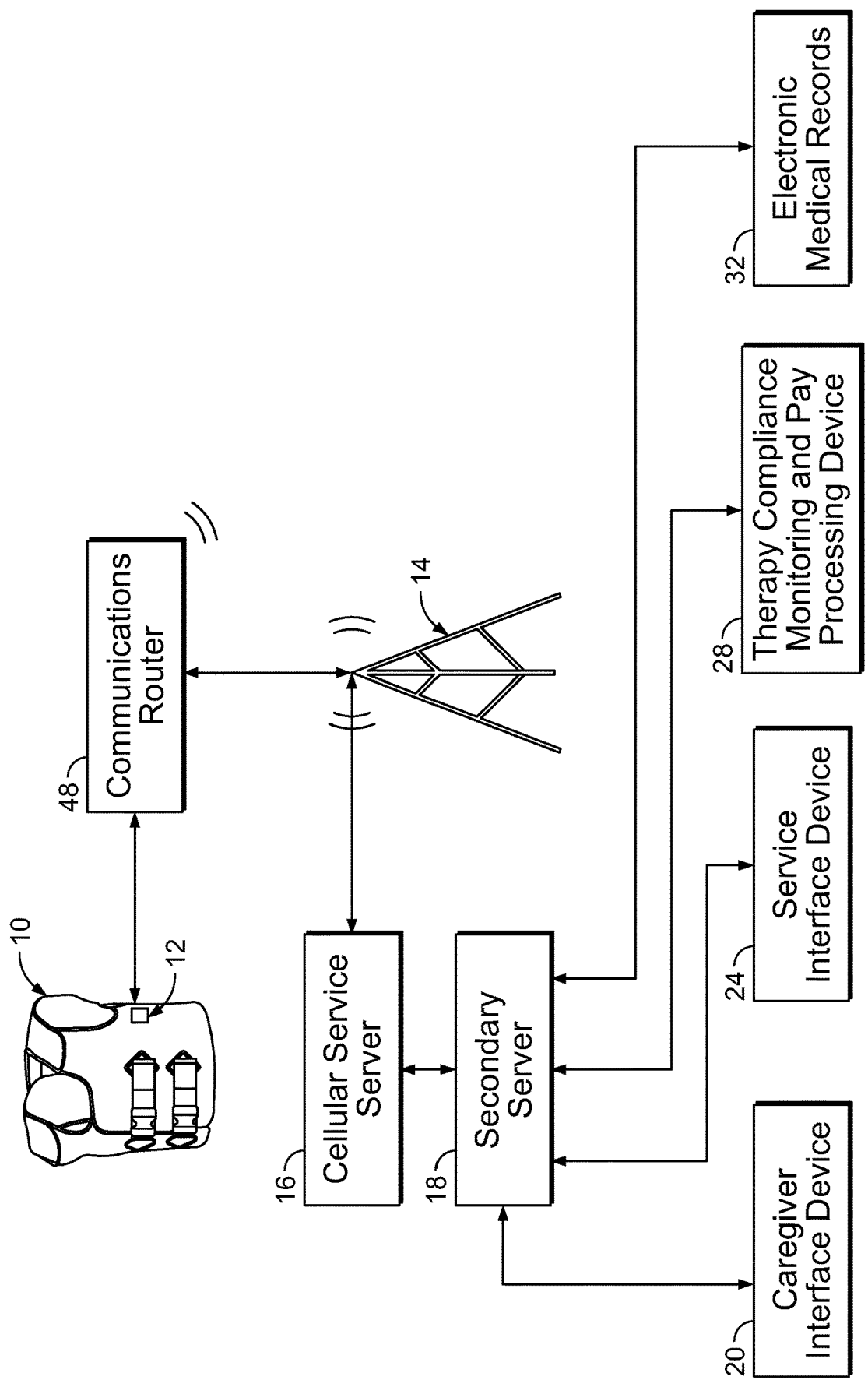
FIG. 4 is a diagram of an HFCWO data connectivity system, according to another embodiment.

FIG. 4 shows another embodiment of data connectivity of a HFCWO system. In the embodiment shown in FIG. 4, the HFCWO controller 12 is mounted on to the HFCWO device 10. The HFCWO controller 12 is configured to communicate with the communications router 48 wirelessly in one embodiment. The communications router 48 is configured to communicate with a cellular service server 16 via a cellular connection in this embodiment via cellular tower 14. The cellular service server 16 is configured to communicate with a secondary server 18 wirelessly in this embodiment while in other embodiments the cellular service server 16 is configured to communicate with a secondary server 18 through a wired connection. Secondary server 18 is configured to transmit data to a caregiver interface device 20, service interface device 24, therapy compliance monitoring and pay processing device 28 and electronic medical records (EMR) 32 in this embodiment wirelessly in this embodiment, while in other embodiments, one or more of the aforementioned data connections may be wired.

Figure 5:
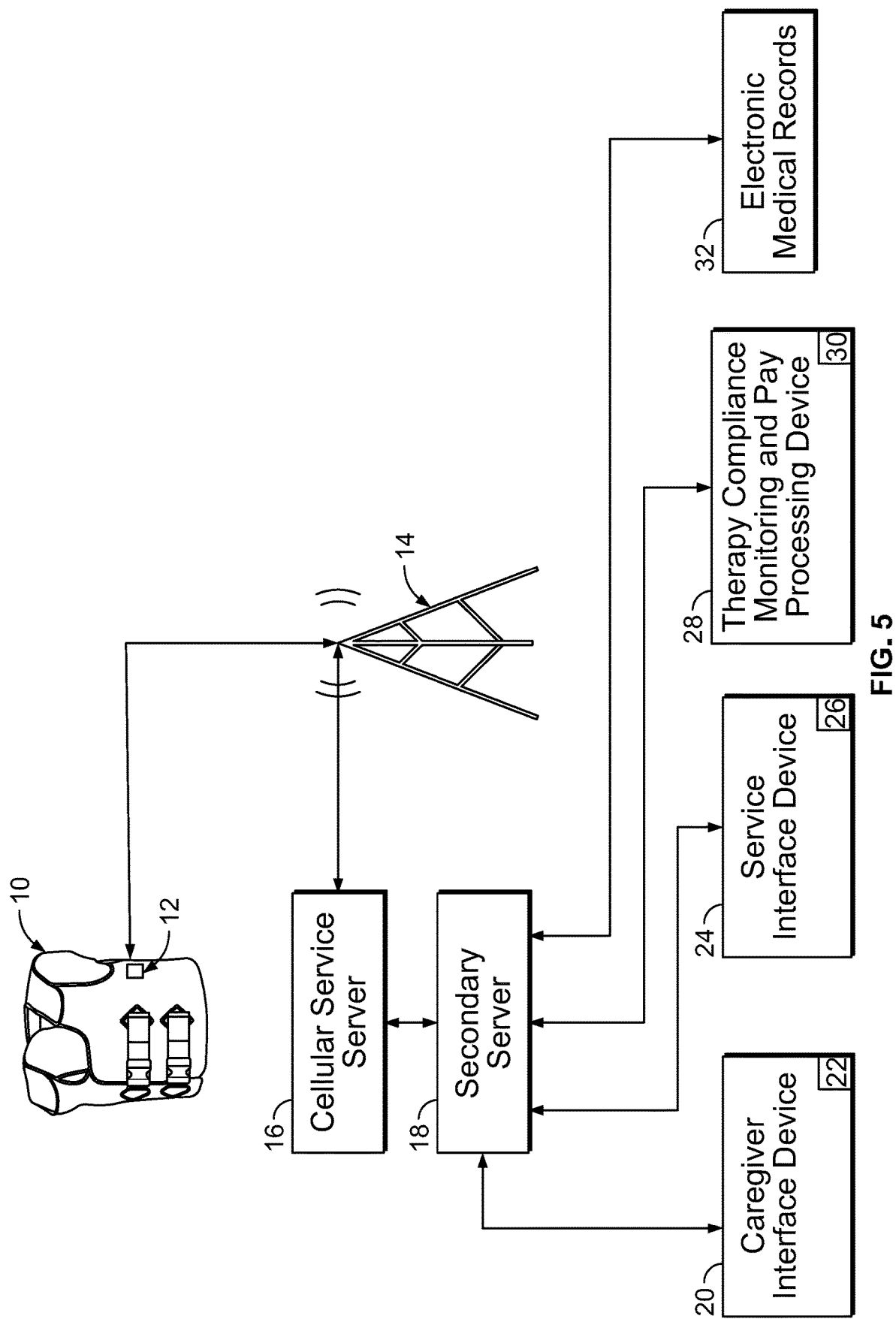
FIG. 5 is a diagram of an HFCWO data connectivity system, according to another embodiment.

FIG. 5 shows one embodiment of an HFCWO system. In the embodiment shown in FIG. 5, the HFCWO controller 12 is mounted on to the HFCWO device 10. In the embodiment shown in FIG. 3, the HFCWO controller 12 includes hardware and/or software configured to communicate with the cellular service server 16 via a cellular connection, in this embodiment by way of cellular tower 14. In the embodiment shown in FIG. 3, the caregiver interface device 20 comprises a caregiver interface display 22 to display information to a caregiver or user. As shown, the service interface device 24 comprises a service interface display 26 to display information related to scheduled and/or unscheduled maintenance. The therapy compliance monitoring and pay processing device 28 comprises a therapy compliance monitoring display 30.

Figure 6:
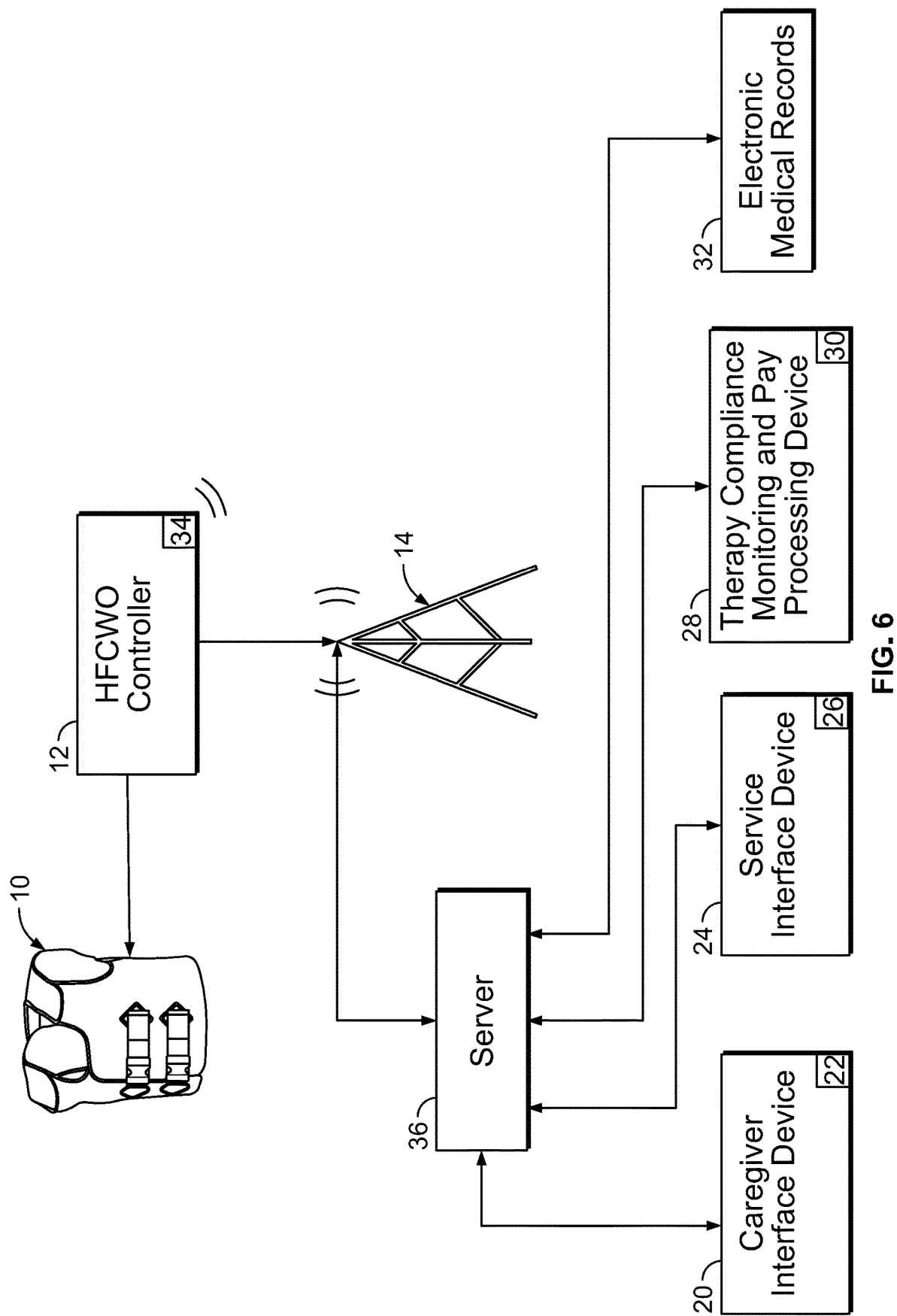
FIG. 6 is a diagram of an HFCWO data connectivity system, according to another embodiment.

FIG. 6 shows another embodiment of an HFCWO data connectivity system. As shown in FIG. 6, a HFCWO controller 12 comprising a HFCWO controller display 34 is configured to control a HFCWO device 10. The HFCWO controller 12 includes hardware and/or software configured to communicate with a server 36 via a cellular connection, in this embodiment by way of cellular tower 14. In the embodiment shown in FIG. 4, the server 36 is configured to communicate with the caregiver interface device 20, service interface device 24, therapy compliance monitoring and pay processing device 28 and electronic medical records (EMR) 32. In the embodiment shown in FIG. 6, the server 36 is configured to perform one or more functions of the cellular service server 16 and the secondary server 18.

While embodiments shown in FIGS. 3-6 describe caregiver interface device 20, service interface device 24, therapy compliance monitoring and pay processing device 28 and electronic medical records (EMR) 32 as physically separate devices, in other embodiments, any one or combination of functions performed by these devices may be performed by one or more devices. In one embodiment, a single device performs all the functions of caregiver interface device 20, service interface device 24, therapy compliance monitoring and pay processing device 28.

Figure 7:
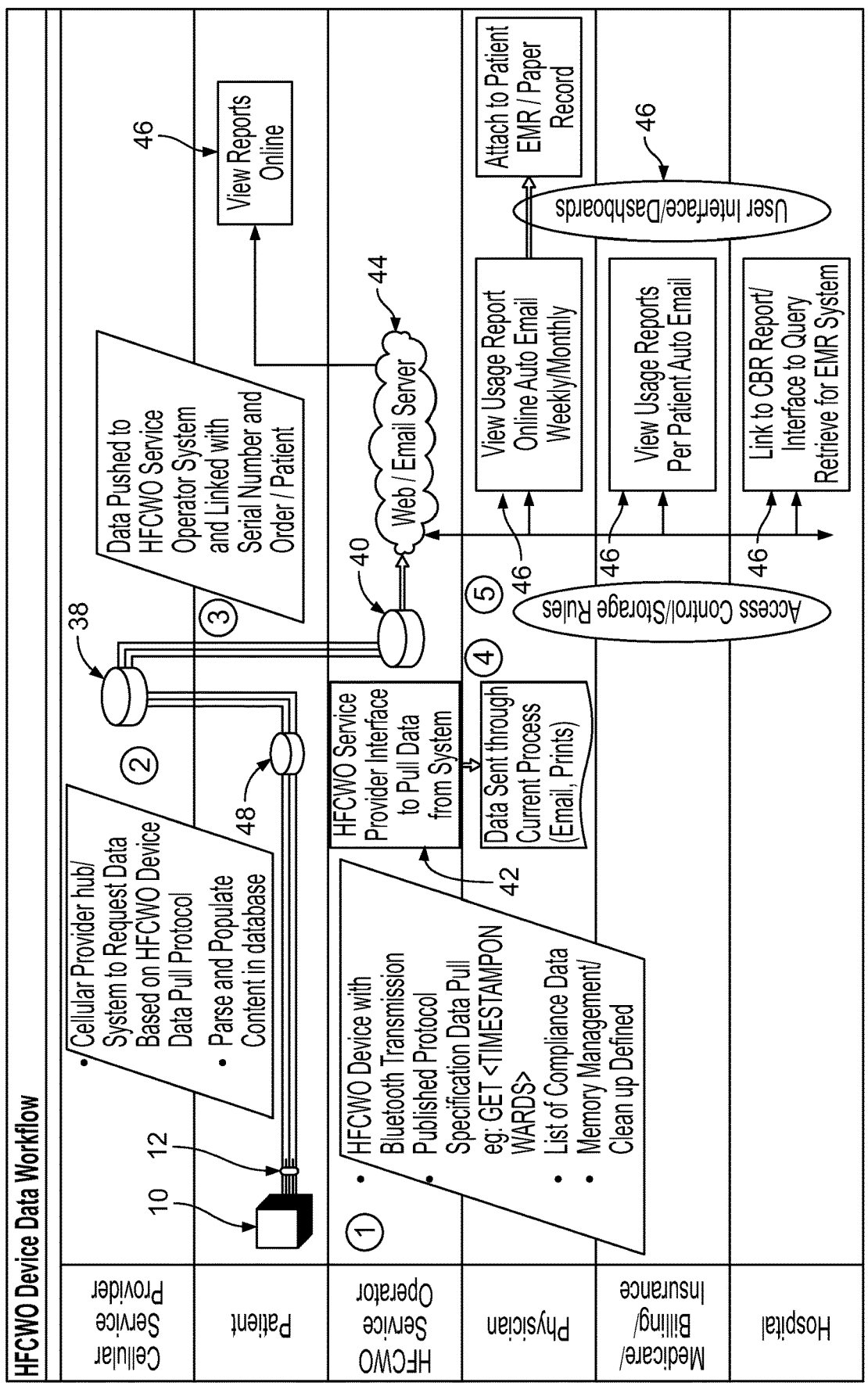
FIG. 7 is a diagram of an HFCWO device data workflow, according to one embodiment.

FIG. 7 shows data flow in one embodiment of an HFCWO system. The HFCWO device 10 is configured to be controlled by a HFCWO controller 12. The HFCWO controller 12 is configured to communicate with a communications router via a wireless connection, in this embodiment using Bluetooth technology. The HFCWO controller 12 stores information related to protocol for data transmission, in this embodiment information related to the time interval when data is to be transmitted. In this embodiment the HFCWO controller 12 is configured to transmit data related to compliance with prescribed therapy, while in another embodiment, the HFCWO controller 12 is configured to store this data on a resident memory device. In this embodiment, the HFCWO controller 12 also stores rules related protocols for memory management and/or data purging of resident memory device.

In the embodiment shown in FIG. 7, the cellular service provider system 38 communicates with and requests data-based on the HFCWO controller 12 data pull protocol via communications router 48. In this embodiment, the HFCWO controller 12 communicates with the communications router 48 via Bluetooth technology and the communications router 48 communicates with the cellular service provider server 38 via a cellular connection. The cellular service provider server 38 parses and populates content received from the HFCWO controller 12 into its database. The cellular service provider server 38 is configured to push data to a secondary server 40 in this embodiment. The cellular service provider server 38 and the secondary server 40 are configured to use the serial number of the HFCWO device 10 and/or a HFCWO controller 12 identifier and/or a patient identifier to transmit data from the cellular service provider server 38 to the appropriate database of the secondary server 40. A HFCWO service provider interface 42 is configured to allow extraction of data from the secondary server 40 in this embodiment which is then accessible to be transmitted using any means including but not limited to e-mails, printing etc. In this embodiment, the secondary server is also configured to communicate data to a web server 44. Web server 44 is configured to provide data to one or more interface devices 46. In this embodiment, the web server 44 is configured to make data available for viewing online by webhosting data and reports. The web server 44 is also configured to provide information at a periodic time interval and, in one embodiment, information specific to a patient, to various interface devices 46 based on storage and/or access control rules. In one embodiment data is supplied to an electronic medical record (EMR) system.

Figure 8:
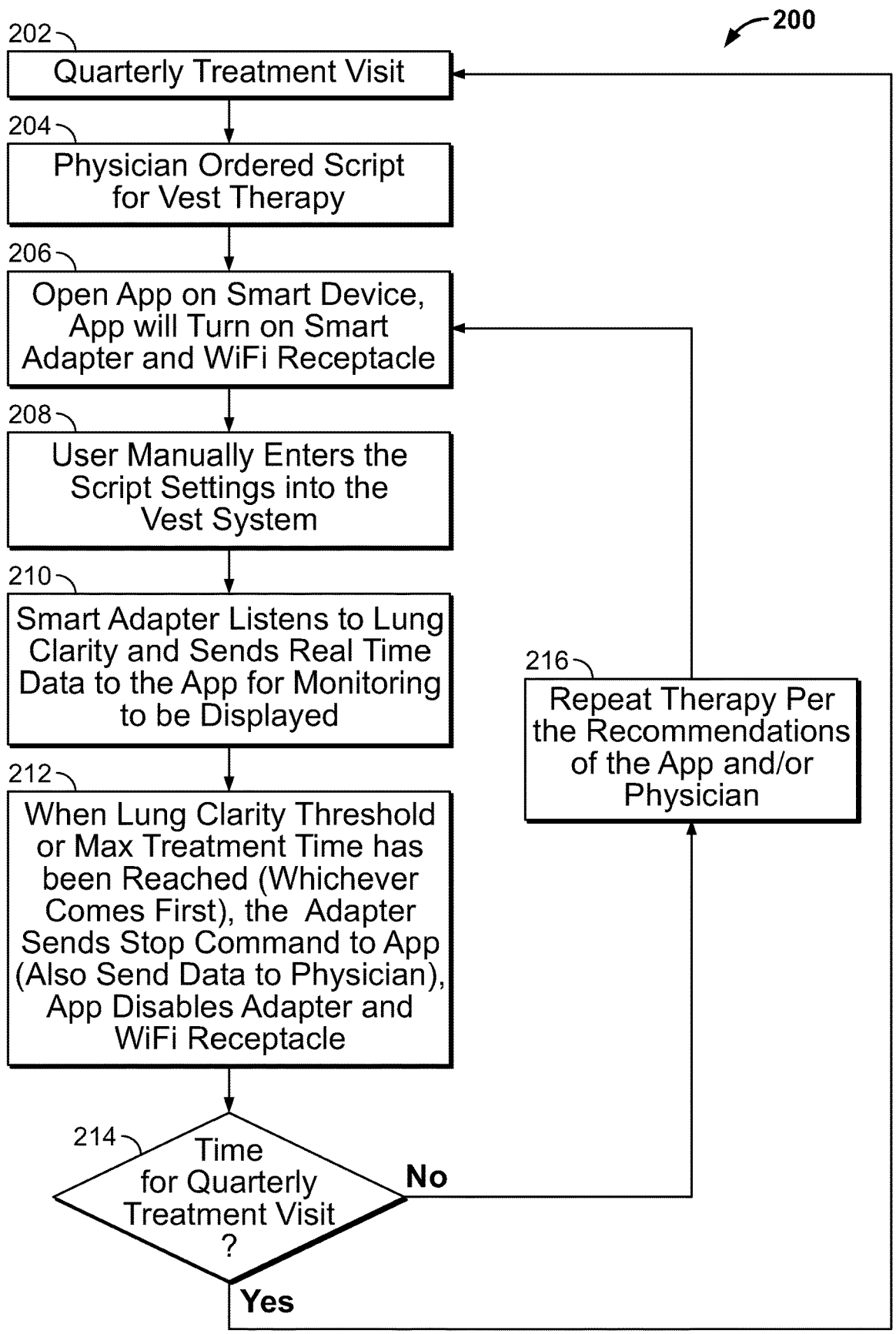
FIG. 8 is a flow chart illustrating a method for sensing a patient's breath sounds and automatically stopping a lung treatment when a threshold is reached, according to one embodiment.

Referring now to FIG. 8, a method 200 for regulating an HFCWO vest using sound analysis is outlined, according to one embodiment. In this embodiment, sound analysis information is used to automatically power off the HFCWO vest when a treatment is complete. Sound analysis data may also be provided to the patient, physician or both, via an application on a smart device (smart phone, tablet, or any other such device) that is wirelessly coupled with a sound sensing device on the vest. The sound sensing device may be one or more microphones, pressure transducers, voice coil actuators or other sound sensing device(s) coupled with the vest, as mentioned previously. In some embodiments, the sound sensing devices may be embedded in or otherwise built into the vest. In alternative embodiments, the sound sensing device (or devices) may be in the form of an adapter (or "smart adapter"), which may be attached to an HFCWO vest that does not have built-in sound sensing capabilities. The embodiment of the smart adapter will be described as part of this embodiment of the method 200, but in alternative embodiments other sound sensing device(s) may be used, any or all of which may be built into an HFCWO vest or attached to an existing HFCWO vest. The smart adapter may be powered by a battery, such as but not limited to a 3.7V LiPo battery (although other sources of power can also be used, such as using air current from the vest pump to turn fan blades to generate electricity), and may contain an internal microphone and Bluetooth module. In one embodiment, the smart adapter has no tethered connections to the HFCWO vest but is only connected to the paired smart device via Bluetooth.

The beginning of the method 200 starts with a patient visiting his or her physician 202, for example as part of a regularly scheduled quarterly lung therapy visit. At the visit, the physician provides a prescription or treatment protocol for the HFCWO vest 204. The physician or patient may then open an application on a smart device 206. The application may communicate with the smart adapter via wireless connection, such as Bluetooth, and it may activate or power on the smart adapter and activate a WiFi receptacle on the smart adapter. Next, the patient, physician, hospital staff or other user may enter settings into the HFCWO vest system 208, in accordance with the physician's prescription or treatment protocol.

When activated, the smart adapter or other sound sensing device senses the patient's lung sounds during breathing 210 and sends real time sensed data to the application on the smart device, where it may be displayed in a format the patient and/or other user can understand. In some embodiments, the smart adapter may sense the patient's lung sounds and process the sensed sound data into a data format the patient and/or physician can read and use. In alternative embodiments, the sensed data may be sent without processing (or with minimal processing) to the application on the smart device, and the application may process the sensed data into a usable/readable data format. Displayed data may include, for example, respiratory rate, a numerical index indicating a volume of the patient's lung sounds, a measured pressure curve or phase shift curve showing the patient's breath cycle, and/or the like.

As the lung treatment with the HFCWO vest progresses, either the lung sounds will reach a level of clarity that corresponds to a predefined threshold clarity (or "target clarity") or the total treatment time prescribed by the physician will elapse. When the earlier of these two events occurs, the sound sensing device(s), such as the smart adapter, may send a stop command to the application to stop the therapy 212. The application may display an indicator and/or provide a sound to the patient, indicating that the lung treatment with the HFCWO vest is complete. The fact that the lung clarity threshold was reached or the treatment was stopped may also be sent to a physician. The application on the smart phone, upon receiving the stop command, may power off the smart adapter and the WiFi receptacle on the smart adapter and thus automatically end the HFCWO vest therapy session. In alternative embodiments, the application itself may generate the stop command, based on data received from the sound sensing device(s). In other alternative embodiments, instead of the application on the smart device automatically powering off the HFCWO vest, the application may simply provide an alert or indicator to the patient, via the smart device, and the patient may manually shut off the HFCWO vest, thus ending the treatment session.

When it is time for a next lung therapy session, the method 200 may next inquire whether it is time for the patient to have another physician visit 214. If not, the patient can repeat the physician prescribed therapy 216 as outlined above, and this will be repeated until a next physician visit. If it is time for a next physician visit, the method 200 starts over again from the beginning. Using this method 200, any given lung treatment using the HFCWO vest may be stopped early, if the patient's lungs reach the predefined clarity threshold or target prescribed by the physician or preset into the vest as a setting. This may save time and prevent unwanted therapy from occurring after the clarity threshold is reached. In other words, the method 200 allows for a more customized lung treatment, based on a patient's actual lung sounds, without requiring the patient to return to the physician after each treatment. In some cases, since the patient's lung sounds are monitored in real time during therapy sessions, a physician might receive at least some of the real time lung sound data from a patient and decide to change the patient's therapy prescription. Although this may require an additional visit by the patient to the physician in some embodiments, it may allow for a more customized, timely approach to therapy than that which occurs with only periodic, scheduled physician visits. Alternatively, in some embodiments the physician may be able to change the therapy prescription via the application on the patient's smart device, such that the patient does not have to make an additional visit to the physician.

Figure 9:
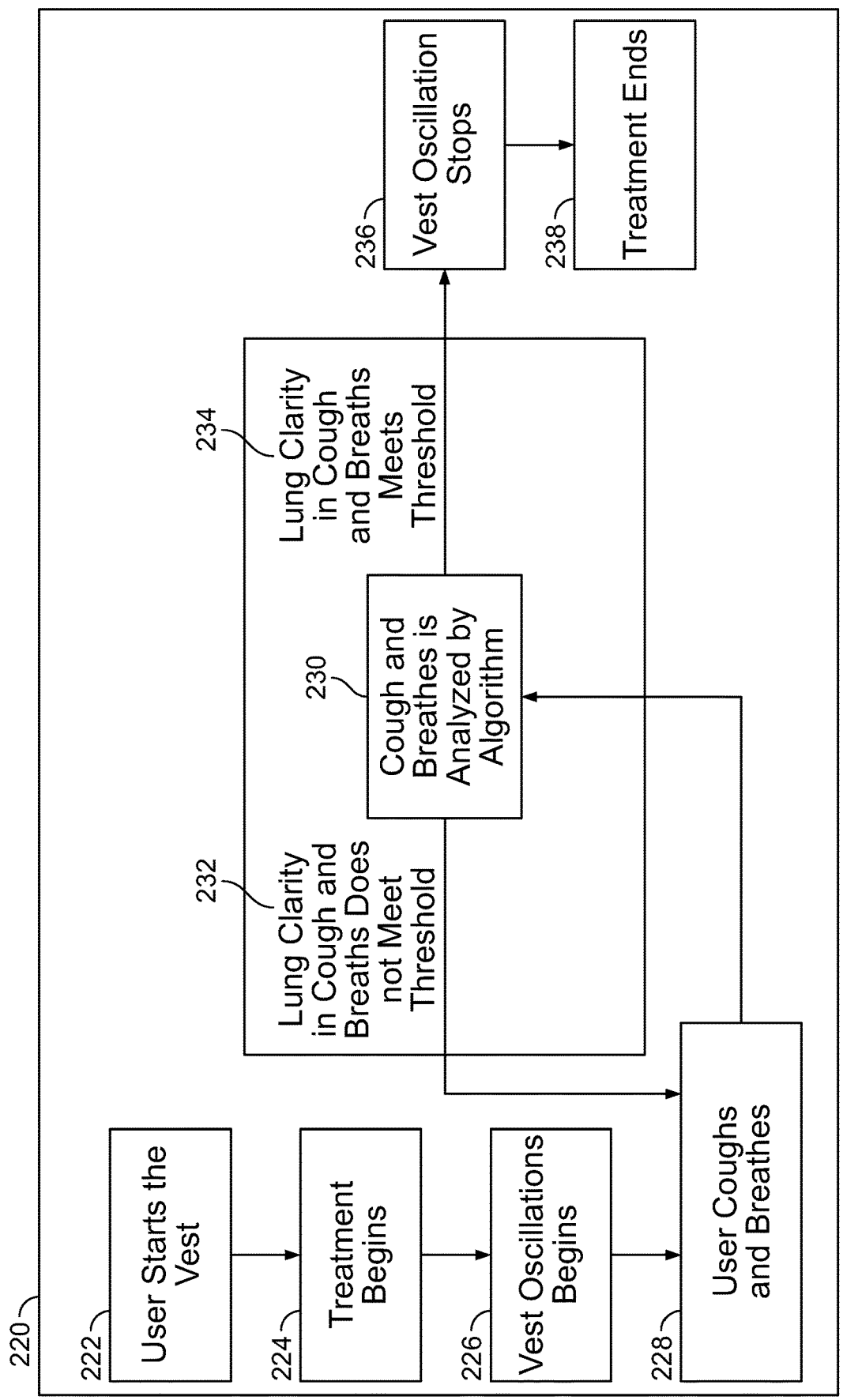
FIG. 9 is a flow chart illustrating a method for sensing a patient's cough and breath sounds and automatically stopping a lung treatment when a threshold is reached, according to another embodiment.

Referring now to FIG. 9, another embodiment of a method 220 for regulating an HFCWO vest using sound analysis is outlined. This embodiment is very similar to the one just described in relation to FIG. 8. In this embodiment, the patient (or physician or other user) first activates the HFCWO vest 222, and the treatment begins 224 with vest oscillation 226. As the treatment begins and progresses, the patient coughs and breathes 228, and the coughing and breathing sounds are sensed via the sound sensing device(s) in the HFCWO vest. These sensed coughing and breathing sounds are then analyzed using an algorithm 230, which may reside in the sound sensing device(s), an application on a smart device, a server or any other suitable location.

If the patient's cough/breathing sounds do not meet a predefined threshold 232, then the lung therapy with the HFCWO vest will continue. If the patient's cough/breathing sounds do meet or exceed the predefined threshold 234, then a stop command will be generated, the HFCWO vest oscillation will stop 236 and the treatment will end 238. The algorithm may use any of a number of data regarding the patient's cough/breathing sounds, such as but not limited to severity of cough/breathing, duration of cough/breaths, type of cough/breaths, number of inhales and exhales and/or respiratory rate. From that data, the algorithm may determine lung clarity and compare the clarity with the predetermined threshold. The algorithm may also optionally provide other information, such as but not limited to lung quality trending (tracking lung performance over time), lung age (comparing the patient's lungs to lungs of a health population) and/or an indicator of treatment progress (indicating how much longer a given treatment will take).

Figure 10:
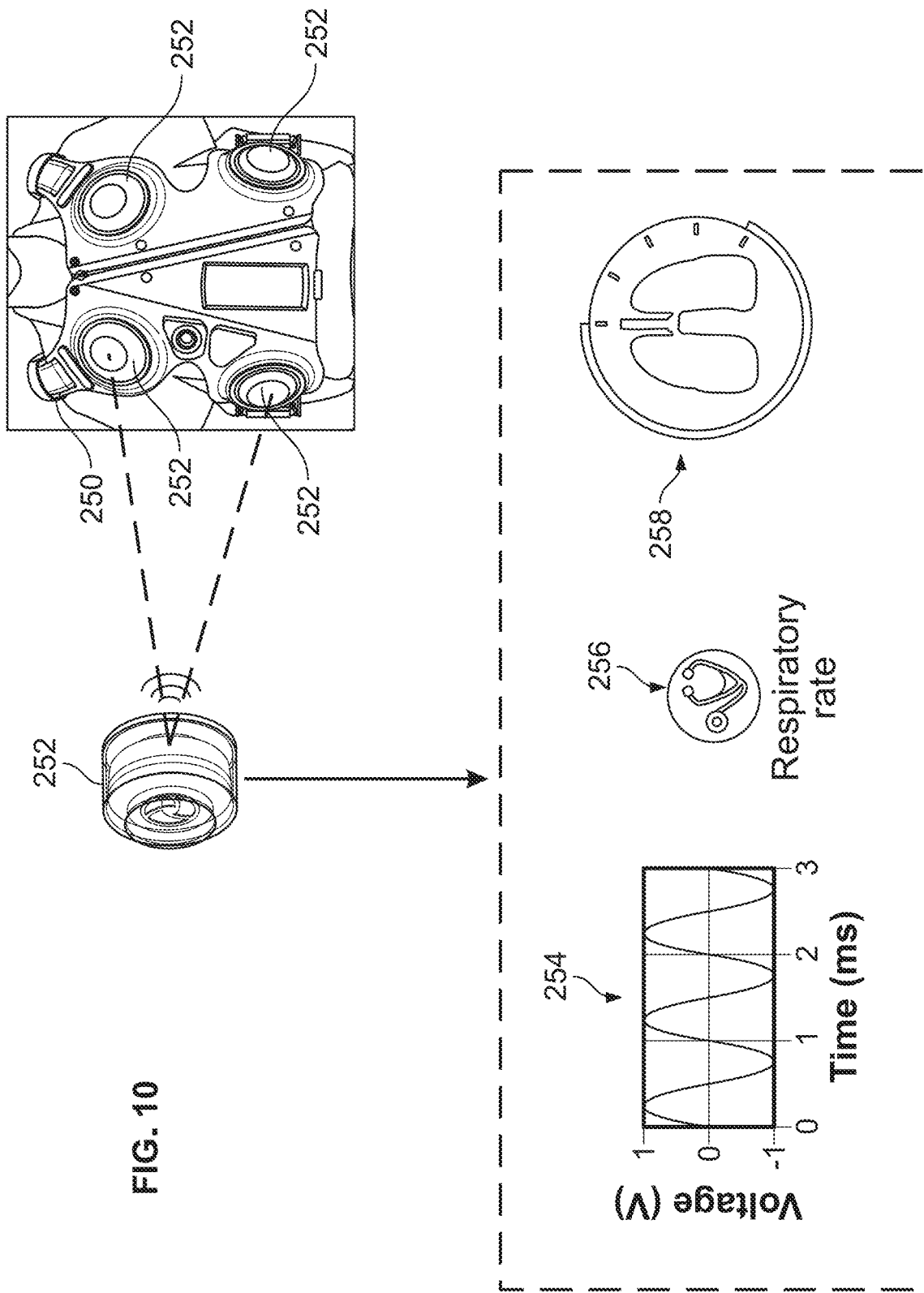
FIG. 10 is a front view of an HFCWO vest with multiple voice coil actuators, along with illustrative metrics for possible display to a user, according to one embodiment.

Referring now to FIG. 10, one exemplary embodiment of an HFCWO vest 250 with multiple VCAs 252 (voice coil actuators) is illustrated. In this embodiment, the HFCWO vest 250 includes four pairs of embedded VCAs 252. Four of the VCAs 252 are embedded in the front of the vest 250, and each one of them has a paired VCA 252 (not visible in FIG. 10) on the back of the vest 250. For each pair of VCAs 252, one acts as a transmitter of signals and the other acts as a receiver. High frequency signals generated by the transmitter VCA 252 pass through the patient's thorax to its paired receiver VCA 252. The VCAs provide percussion therapy on the patient's thorax and also allow the vest 250 to monitor phase shifts in the transmitted and received signals. These phase shifts can be analyzed via an algorithm to provide lung function data. The voltage of the received signal over time can be traced as a curve 254, and the different curves of the different pairs of VCAs 252 can be used over time to monitor the patient's breath sounds, for example as phase shifts. The HFCWO vest 250 and its VCAs 252 may also be used to monitor respiratory rate 256 and/or timing of a therapy session 258.

Figure 11A:
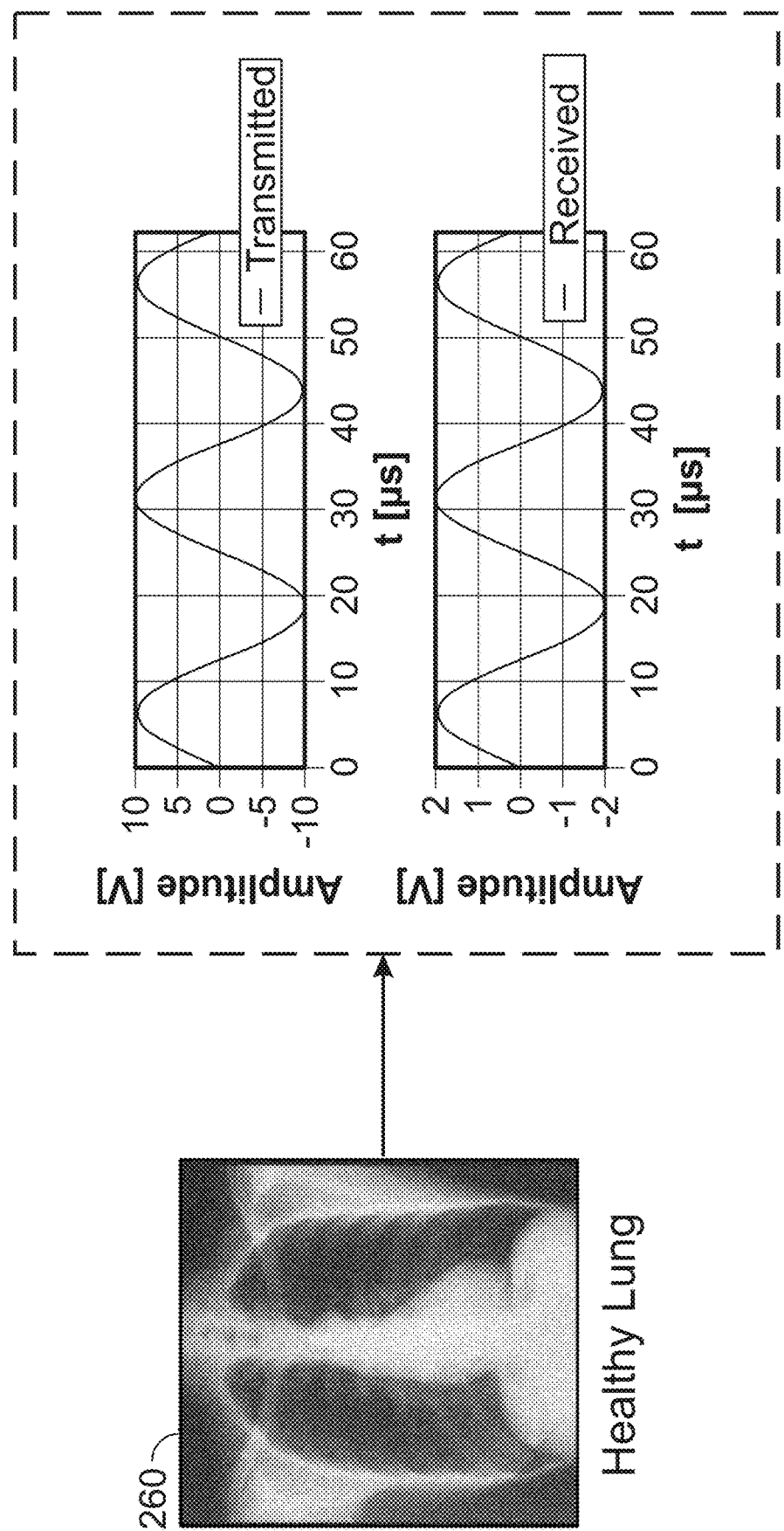
FIG. 11A is a radiograph of a patient's thorax with healthy lungs and tracings from a transmitter and a receiver, according to one embodiment.
Figure 11B:
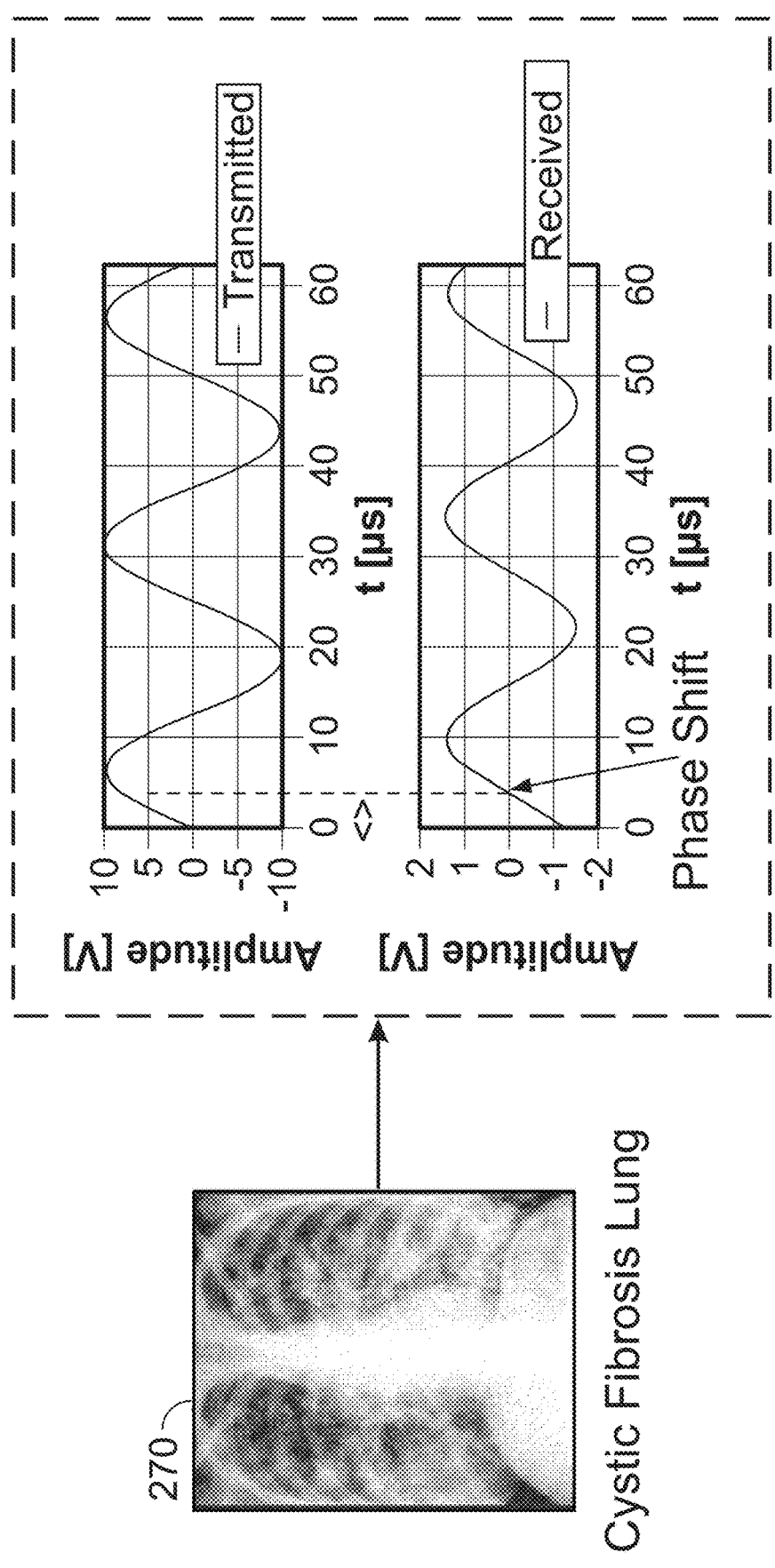
FIG. 11B is a radiograph of a patient's thorax with cystic fibrosis lungs and tracings from a transmitter and a receiver, according to one embodiment.

Referring to FIGS. 11A and 11B, one example of the ways in which the HFCWO vest of FIG. 10 may be used is illustrated. In FIG. 11A, a radiograph 260 (or "X-ray") of a normal chest and lungs is show in the left panel. The right panel shows two tracings: the top tracing 262 shows the amplitude of a transmitted signal from a transmitter VCA 252 over time. The bottom tracing 264 shows the amplitude of a received signal from a receiver VCA 252 over the same time period. As the two tracings 262, 264 illustrate, the phases of the curves are in synch with one another, and the amplitudes are the same in both. By contrast, FIG. 11B shows, in the left panel, a radiograph 270 a patient's lungs with cystic fibrosis. In the right panel, the top tracing 272 again shows the transmitted signal, and the bottom tracing 274 shows the received signal. The bottom tracing 274 shows that there is a lag time between the transmitted and received signal, and the received signal also has a lower amplitude than the transmitted signal. In other words, there is a phase shift in the received signal versus the transmitted signal. This phase shift may be provided to a patient and/or physician in the form of a curve or other data to indicate the presence of mucus in the patient's lungs. In some embodiments, the level of the phase shift may also be used to quantify or approximate an amount and/or viscosity of mucus in the lungs.

Figure 12:
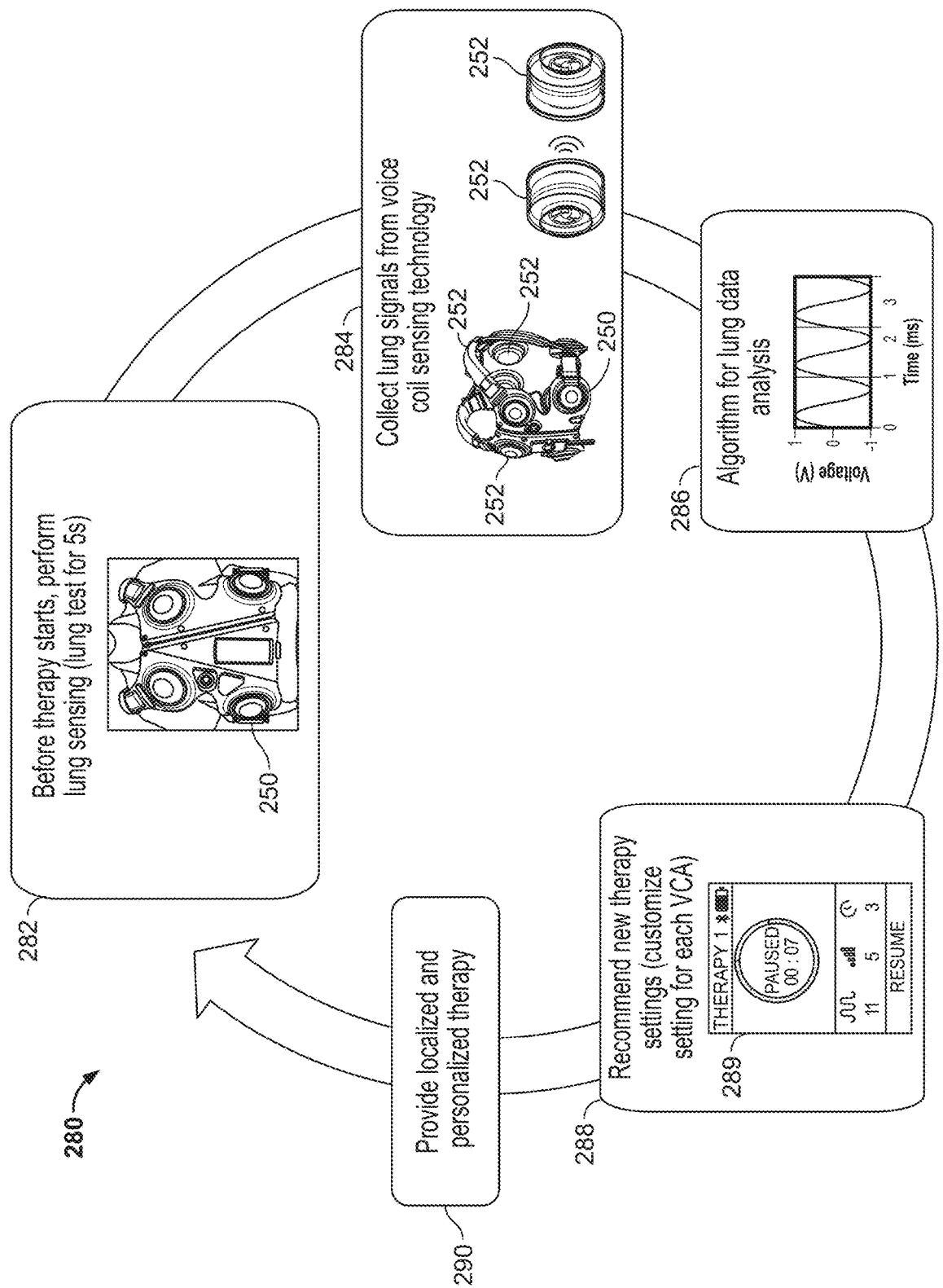
FIG. 12 is an illustration of a system and method for sensing a patient's breath sounds and providing customized therapy recommendations, according to one embodiment.

Referring now to FIG. 12, another embodiment of a method 280 for using the HFCWO vest 250 to monitor breath sounds and customize therapy is illustrated. At the beginning of the method 280, before therapy starts, the HFCWO vest 250 with its VCAs 252 may be used to sense the patient's lung sounds 282 for a short period of time, such as five or ten seconds. The therapy is then started, and the vest 250 and VCAs 252 are used to collect lung signals from the patient 284. The sensed lung signals 286 are then analyzed 286, using an algorithm, and this analysis is used to provide recommended new therapy settings 288. In some embodiments, for example, settings may be customized for each VCA pair. Analyzed lung signal data may also be provided on a display 289, for example on a smart device of the patient and/or physician. The illustrated display 289, for example, shows the progress and remaining time of the therapy session, a setting of the therapy, and that the session is paused. This data and/or any other suitable data may be displayed, according to various embodiments. Finally, the method may involve providing a localized and personalized therapy prescription 290 for the patient for future therapy sessions.

Figure 13:
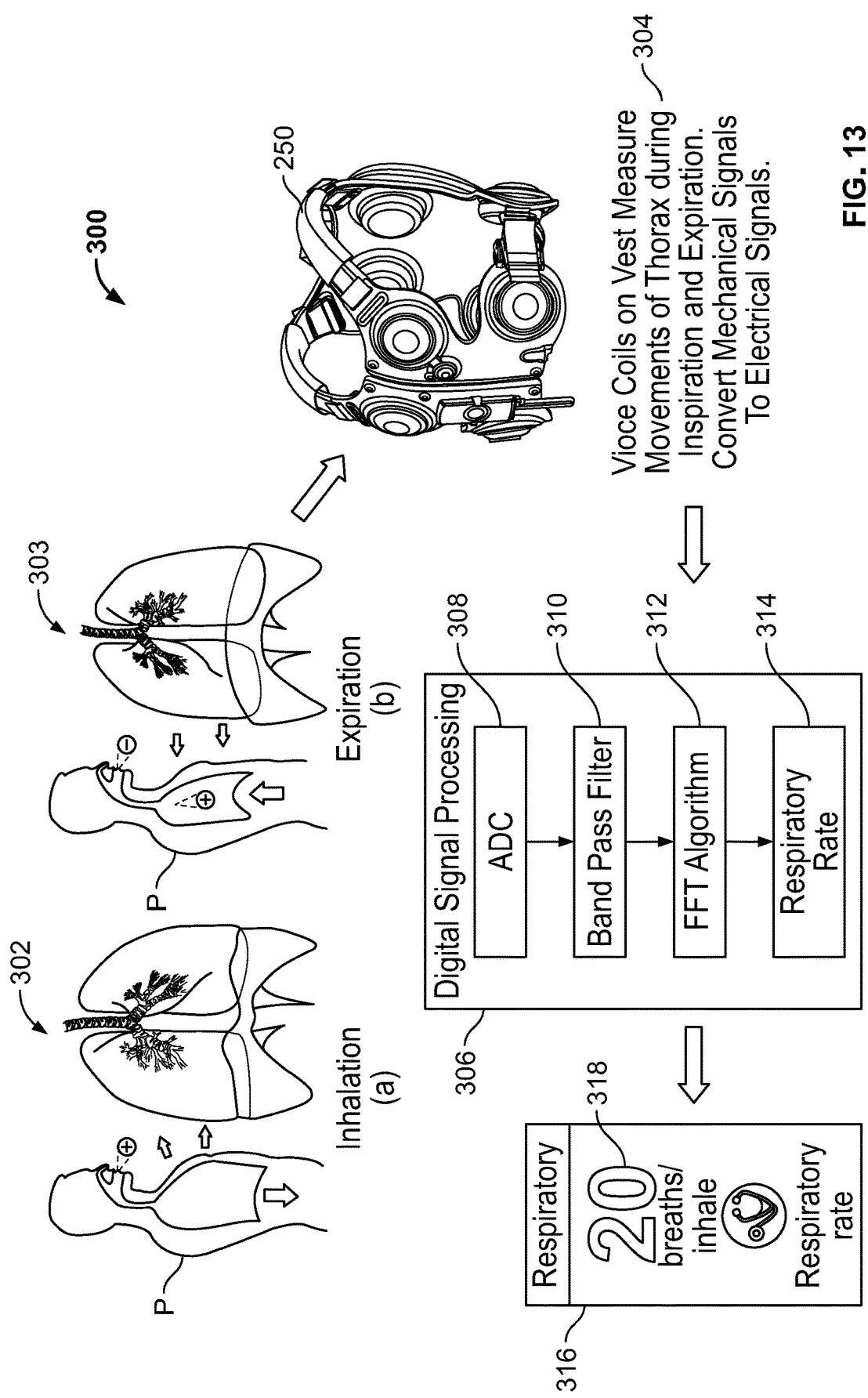
FIG. 13 is an illustration of a system and method for sensing a patient's breath sounds and providing customized therapy recommendations, according to one embodiment.

Referring now to FIG. 13, another embodiment of a method 300 for using the HFCWO vest 250 with VCAs 252 is illustrated. As mentioned previously, in some embodiments, the HFCWO vest 250 may be used to measure the patient's respiratory rate. For example, the VCAs 252 in the described embodiment of the HFCWO vest 250 are sensitive enough to detect mechanical movement and vibration of a patient's chest wall, and this sensed movement can be used to extrapolate the respiratory rate.

In the embodiment of the method 300 illustrated in FIG. 13, a patient P wears the HFCWO vest 250. As the patient inhales 302 and exhales 303 the VCAs on the vest 250 measure movements of the patient's thorax 304. The VCAs 252 convert mechanical signals to electronic signals, and those signals are sent to a digital signal processing module 306, which may be housed on or off the vest 250. In this embodiment, electronic signals pass through an analog-to-digital converter 308, a band pass filter 310, and a Fast Fourier Transform (FFT) algorithm 312, to provide the respiratory rate 314. The patient's measured respiratory rate 318 may then be provided to a user on a display 316. A similar analytical method may be used to measure the patient's effort of breathing, and in various embodiments both the respiratory rate and the breathing effort may be displayed.

The use of the terms "a" and "an" and "the" and similar referents in the context of describing the subject matter (particularly in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Furthermore, the foregoing description is for the purpose of illustration only, and not for the purpose of limitation, as the scope of protection sought is defined by the claims as set forth hereinafter together with any equivalents thereof entitled to. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the invention as claimed.

What is claimed is:

1. A respiratory therapy and analysis system for administering a percussive treatment and sensing and analyzing respiratory sounds of a patient, the system comprising:
   a high frequency chest wall oscillation (HFCWO) vest;
   at least one sensor coupled with the HFCWO vest, the at least one sensor including at least one pair of voice coil actuators having a transmitter voice coil actuator that transmits a signal on a first side of the HFCWO vest, and a receiver voice coil actuator that receives the signal on a second side of the HFCWO vest; and
   an algorithm stored in a processor for processing sensed data from the at least one sensor to provide processed data describing the respiratory sounds of the patient, in a form that is usable by a user, wherein the respiratory sounds are used by the algorithm to determine lung clarity, and the percussive treatment is stopped when the lung clarity reaches a predefined threshold or a prescribed treatment time elapses, whichever occurs first, and the lung clarity is determined by measuring a phase shift in the signal received by the receiver voice coil actuator.

2. The system of claim 1, wherein the at least one pair of voice coil actuators comprises multiple pairs of voice coil actuators.

3. The system of claim 2, wherein the multiple pairs of voice coil actuators are configured to provide the percussive treatment to the patient.

4. The system of claim 1, wherein the algorithm comprises a machine learning algorithm.

5. The system of claim 1, wherein the algorithm comprises:
   a pre-processing function;
   a feature extraction function; and
   a classification function.

6. The system of claim 1, wherein the form of the processed data is selected from the group consisting of a patient progress report, a pulmonary function test report, and environmental data affecting breathing.

7. The system of claim 1, further comprising a charger main control board coupled with the at least one sensor, wherein the charger main control board comprises:
   a digital signal processor; and
   a radiofrequency module.

8. A respiratory analysis system for sensing and analyzing respiratory sounds of a patient, the system comprising:
   at least one acoustic sensor for attaching to a high frequency chest wall oscillation (HFCWO) vest, the at least one acoustic sensor having at least one pair of voice coil actuators that includes a transmitter voice coil actuator configured to transmit a signal on a first side of the HFCWO vest, and a receiver voice coil actuator configured to receive the signal on a second side of the HFCWO vest; and
   an algorithm stored in a processor for processing sensed acoustic data from the at least one acoustic sensor to provide processed data describing the respiratory sounds of the patient, in a form that is usable by a user, wherein the respiratory sounds are used by the algorithm to determine lung clarity, and a percussive treatment is stopped when the lung clarity reaches a predefined threshold or a prescribed treatment time elapses, whichever occurs first, and the lung clarity is determined by measuring a phase shift in the signal received by the receiver voice coil actuator.

9. The system of claim 8, wherein the processor is housed in the HFCWO vest or another computing device.

10. The system of claim 8, further comprising an application for a smart device, configured to display at least one indicator to the patient regarding at least one of a lung function of the patient's lungs or progress of a lung treatment being performed on the patient's lungs.

11. A method for measuring and analyzing respiratory sounds of a patient's lungs, the method comprising:
   sensing at least one of respiratory sounds or chest wall movement, using at least one sensor coupled with a high frequency chest wall oscillation (HFCWO) vest, the at least one sensor including a transmitter voice coil actuator and a receiver voice coil actuator, and sensing the at least one of the respiratory sounds or the chest wall movement including transmitting a signal from the transmitter voice coil actuator on a first side of the HFCWO vest, and receiving the signal with the receiver voice coil actuator on a second side of the HFCWO vest;
   converting sensed data from the patient's lungs to electronic data;
   processing the electronic data to provide lung function assessment data by measuring a phase shift between the transmitted signal and the received signal;
   providing the lung function assessment data to a user;
   determining whether the patient's breathing is at or above a predetermined threshold clarity based on the lung function assessment data; and
   automatically stopping a percussive treatment when the patient's breathing reaches the predetermined threshold clarity or a prescribed treatment time elapses, whichever occurs first.

12. The method of claim 11, wherein the sensing step comprises sensing chest wall movement with at least one of the transmitter voice coil actuator and the receiver voice coil actuator, and wherein the providing step comprises providing a respiratory rate.

13. The method of claim 11, further comprising providing an adjusted HFCWO treatment prescription, based on the lung function assessment data.

14. The method of claim 11, wherein providing the lung function assessment data comprises displaying the lung function assessment data on a display of a smart device.

15. The system of claim 1, further comprising a smart device, and wherein completion of the percussive treatment with the HFCWO vest is displayed on the smart device.

* * * * *